US009726877B2

(12) United States Patent
Kleppe et al.

(10) Patent No.: US 9,726,877 B2
(45) Date of Patent: Aug. 8, 2017

(54) HIGH-RESOLUTION LUMINESCENCE MICROSCOPY

(71) Applicant: Carl Zeiss Microscopy GmbH, Jena (DE)

(72) Inventors: Ingo Kleppe, Jena (DE); Yauheni Novikau, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 232 days.

(21) Appl. No.: 14/350,919

(22) PCT Filed: Oct. 11, 2012

(86) PCT No.: PCT/EP2012/070215
§ 371 (c)(1),
(2) Date: Apr. 10, 2014

(87) PCT Pub. No.: WO2013/053859
PCT Pub. Date: Apr. 18, 2013

(65) Prior Publication Data
US 2015/0035964 A1    Feb. 5, 2015

(30) Foreign Application Priority Data
Oct. 12, 2011   (DE) .................. 10 2011 084 315

(51) Int. Cl.
G02B 21/36     (2006.01)
G02B 21/16     (2006.01)
(Continued)

(52) U.S. Cl.
CPC ....... *G02B 21/367* (2013.01); *G01N 21/6458* (2013.01); *G02B 21/0076* (2013.01);
(Continued)

(58) Field of Classification Search
CPC .... G02B 21/367; G02B 21/16; G02B 21/361; G02B 21/0076; G02B 27/58; G01N 21/6458; G06F 3/044; G06F 3/0412
(Continued)

(56) References Cited

U.S. PATENT DOCUMENTS

| 6,909,105 | B1 * | 6/2005 | Heintzmann | G02B 21/00 250/550 |
| 2009/0237501 | A1 * | 9/2009 | Lemmer | G01N 21/6458 348/79 |
| 2010/0303386 | A1 * | 12/2010 | Enderlein | G02B 21/367 382/299 |

FOREIGN PATENT DOCUMENTS

DE    199 08 883 A1    9/2000
DE    10 2008 054 317 A1    5/2010
(Continued)

OTHER PUBLICATIONS

Geissbuchler, Stefan, et al., "Comparison between SOFI and STORM", Biomedical Optics Express 2011, 2(3):408-420.
(Continued)

*Primary Examiner* — Thai Tran
*Assistant Examiner* — Nien-Ru Yang
(74) *Attorney, Agent, or Firm* — Duane Morris LLP (57) ABSTRACT

A microscopy method for producing a high-resolution image of a sample which includes furnishing the sample with a marker that emits statistically flashing luminescence radiation after excitation, or using a sample that has molecules that emit statistically flashing luminescence radiation after excitation. The sample is excited to luminescence in such a manner that the marker/molecules emit luminescence radiation flashing at a flash rate, wherein—the illumination is structured in such a manner that the flash rate varies locally and—the sample is repeatedly illuminated in different illumination states of the structured illumination. The luminesc-
(Continued)

ing sample is repeatedly imaged on a detector in each of the different illumination states.

16 Claims, 4 Drawing Sheets

(51) Int. Cl.
*G02B 21/00* (2006.01)
*G01N 21/64* (2006.01)
*G02B 27/58* (2006.01)
*G06F 3/041* (2006.01)
*G06F 3/044* (2006.01)

(52) U.S. Cl.
CPC ........... *G02B 21/16* (2013.01); *G02B 21/361* (2013.01); *G02B 27/58* (2013.01); *G06F 3/044* (2013.01); *G06F 3/0412* (2013.01)

(58) Field of Classification Search
USPC .......................................................... 348/79
See application file for complete search history.

(56) References Cited

FOREIGN PATENT DOCUMENTS

| DE | 10 2008 059 328 A1 | 6/2010 |
|---|---|---|
| EP | 1 157 297 B1 | 11/2002 |
| WO | WO 2009/115108 A1 | 9/2009 |
| WO | WO 2010/141608 A1 | 12/2010 |
| WO | WO 2012/168065 A1 | 12/2012 |

OTHER PUBLICATIONS

Dertinger, Thomas, et al., "Achieving increased resolution and more pixels with Superresolution Optical Fluctuation Imaging (SOFI)" Optics Express 2010, 18(18):18875-18885.

Dertinger, T., et al., "Fast, background-free, 3D super-resolution optical fluctuation imaging (SOFI)", PNAS 2009, 106(52):22287-22292.

Gustafsson, Mats G.L., "Nonlinear structured-illuminated microscopy: Wide-field fluorescence imaging with theoretically unlimited resolution", PNAS 2005, 102(37):13081-13086.

Heintzmann, R., et al., "Laterally Modulated Excitation Microscopy: Improvement of resolution by using a diffraction grating", SPIE, 3568:185-196.

Muller, Claus B., et al., "Imaging Scanning Microscopy", Physical Review Letters 2010, 104:198101-1-198101-4.

Van de Linde,S.,et al.,"Photoinduced formation of reversible dye radicals and their impact on super-resolution imaging", Photochemical&Photobiological Sciences 2010,10:499-506.

\* cited by examiner

HIGH-RESOLUTION LUMINESCENCE MICROSCOPY

RELATED APPLICATIONS

The present application is a U.S. National Stage application of International PCT Application No. PCT/EP2012/070215 filed on Oct. 11, 2012 which claims priority benefit of German Application No. DE 10 2011 084 315.9 filed on Oct. 12, 2011, the contents of each are incorporated by reference in their entirety.

FIELD OF THE INVENTION

The invention relates to a microscopic method or a microscope for generating a high-resolution image of a luminescing sample.

BACKGROUND OF THE INVENTION

The analysis of samples by means of microscopy is a broad technical field for which a variety of technical solutions are available. Various microscopic methods have been developed on the basis of traditional light-optical microscopy, Luminescence microscopy is a traditional field of application of light-optical microscopy for examining biological preparations. In so doing, certain dyes (also known as phosphors or fluorophores) are used for the specific marking of samples, e.g. of parts of cells. As mentioned, the sample is illuminated with excitation radiation and the luminescent light excited in this fashion detected with suitable detectors. A dichroic beam splitter combined with block filters is commonly provided in the light-optical microscope for this purpose, to separate the fluorescence radiation from the excitation radiation, thus allowing a separate observation. This approach makes it possible to reproduce individual, differently stained parts of cells in the light-optical microscope. Obviously, a plurality of parts of a preparation can be stained simultaneously with varying dyes that adhere specifically to different structures of the preparation. This method is known as multicolor luminescence. Furthermore, samples can be analyzed that are luminescent per se, i.e. without the addition of markers.

As is common, luminescence as used herein refers to the generic term for phosphorescence and fluorescence, meaning that it comprises both processes.

Moreover, the use of laser scanning microscopy (also known with the abbreviation LSM) has been disclosed. It only reproduces the plane located in the focal plane of a lens from a three-dimensionally illuminated image by means of a confocal detection arrangement (referred to as confocal LSM) or a nonlinear sample interaction (so-called multiphoton microscopy). An optical section is obtained and the documentation of a plurality of optical sections in various depths of the sample then makes it possible to generate a three-dimensional image of the sample by means of suitable data processing equipment, said image being composed of different optical sectional views. As a result, laser scanning microscopy is suitable for examining thick preparations.

Different approaches have recently been developed for resolutions beyond the diffraction limit, which is determined by the laws of physics. Said microscopic methods are characterized in that they provide the user with a higher lateral and/or axial optical resolution compared with a conventional microscope. In the description at hand, these kinds of microscopic methods are referred to as high-resolution microscopic methods, because they achieve a resolution beyond the optical diffraction limit. In contrast, microscopes with limited diffraction limits are referred to as conventional microscopes. They are used to realize known optical wide-field microscopy or laser scanning microscopy.

A high-resolution microscopic method is disclosed in EP 1157297 B1. In it, nonlinear processes are utilized by means of structural illumination. Fluorescence saturation serves as nonlinearity. The spectrum of lens space is displaced relative to the transmission function of the optical system through structured illumination. In detail, the displacement of the spectrum means that the lens space frequencies V0 are transmitted at a space frequency V0-Vm, wherein Vm is the structured illumination frequency. With the given maximum space frequency the system is able to transmit, this enables the transfer of space frequencies of the object that exceed the maximum frequency of the transmission function by the displacement frequency Vm. Fourier filtering as reconstruction algorithm for imaging and the use of a plurality of shots for one image are required for this approach. Structured wide-field illumination of the sample, for example through an amplitude/phase screen, is hence used in EP 1157297 B1, which is likewise fully taken into account with regard to the corresponding description of the resolution microscopy method. Fluorescence in the sample is again detected by wide-field microscopy. The screen is now brought into three different rotary positions, e.g. 0°, 120° and 240°, and in each rotary position, the screen is moved to three or more different positions. The sample is detected by wide-field microscopy for each of the three displacements of the three rotary positions (for a total of at least 9 illumination states). Furthermore, the screen has frequencies that are as close as possible to the limit frequency the used optical arrangement is capable of transmitting. The mentioned displacement subsequently takes place with the use of Fourier filtering, whereby in particular the zeroth and +/− first order of diffraction in the images is evaluated. Said microscopic method is also known as SIM method.

An increase in resolution is obtained with this principle if the intensity of the structuring (e.g. through a screen) is such that the fluorescence of the sample reaches saturation in the bright area. In that case, the structured illumination of the sample no longer has a sinusoidal distribution on the sample, but even higher order harmonics beyond the optical limit frequency due to the saturation effects. Said upgrade of the SIM method is also known as saturated patterned excitation microscopy (SPEM).

An upgrade of the SIM method can also be achieved with a linear illumination arranged perpendicular to the direction of the screen. This creates a line of illumination, whereby the screen structure is reflected along the line. In other words, the lines of the illumination are structured by the screen. The linear illumination allows a confocal slit detection and hence a further increase in resolution. Said method is also known as SLIM.

The publication by C. Muller and J. Enderlein titled "Image scanning microscopy", Physical Review Letters, 104, 198101 (2010) is based on the SIM principle, although it scans the sample using confocal illumination and detection, followed by Fourier filtering. Said principle is also known as ISM. It does not involve nine orientations of a structured illumination, but each scan position, i.e. each scanning state during the scanning of an image corresponds to an illumination state, and the structured illumination is a spot illumination of the sample.

Another high-resolution method of luminescence microscopy is disclosed in the publication by T. Dertinger, et al., titled "Fast, background-free, 3D super-resolution optical fluctuation imaging (SOFI)", PNAS (2009), p. 22287-22292 as well as "Achieving increased resolution and more pixels with Superresolution Optical Fluctuation Imaging (SOFI)", Opt. Express, Aug. 30, 2010, 18 (18): 18875-85, doi: 10.1364/IE.18.018875 and S. Geissbuehler et al., "Comparison between SOFI and STORM", Biomed. Opt. Express 2, 408-420 (2011). Said method is utilizing the blinking properties of a fluorophore. If the fluorophores of a sample are statistically blinking independently from each other, a considerable increase in resolution of the illustrated sample beyond the optical resolution limit defined by the laws of physics can be achieved by way of suitable filtering using a so-called cumulant-generating function. One example of said type of cumulant-generating function includes the second-order autocorrelation function. To generate a high-resolution image, it involves the recording of a series of individual images and the subsequent amalgamation into a single image by means of the cumulant-generating function, said single image then having the higher resolution. Said method is referred to as "Super-Resolution Optical Fluctuation Imaging" or SOFI method for short.

Based on the prior art, it is also known to combine a plurality of high-resolution microscopy methods. For example, the combination of a variety of high-resolution microscopy methods is described in DE 102008054317 A1, with the purpose of using the optimal method for individual sample areas, in each case taking into account the resolution and measuring speed.

OBJECTS OF THE INVENTION

An object of the invention is to provide a microscopic method or a microscope that achieves an increased resolution.

SUMMARY OF THE INVENTION

According to the invention, a microscopic method is provided for generating a high-resolution image of a sample, wherein a) the sample is provided with a marker that emits statistically blinking luminescent radiation after excitation, or a sample is used, which has molecules that emit statistically blinking luminescent radiation after excitation, b) the sample is excited to luminescence by structured illumination such that the markers/molecules emit luminescent radiation blinking at a blinking rate, wherein the illumination is structured such that the blinking rate varies locally and the sample is illuminated repeatedly in different illumination states of the structured illumination, such that a different local distribution of the blinking rate is obtained for each illumination state, c) the luminescing sample is imaged repeatedly on a detector in each of the different illumination states, such that an image sequence is obtained for each of the different illumination states, d) a raw image reproducing the local distribution of the blinking rate in the sample is generated from each image sequence, e) the high-resolution image, which has a spatial resolution greater than that of the image on the detector, is generated from the obtained raw images by computational processing comprising Fourier filtering.

Furthermore, a microscope is provided for generating a high-resolution image of a sample, wherein the sample is provided with a marker that emits statistically blinking luminescent radiation after excitation, or a sample that comprises molecules that emit statistically blinking luminescent radiation after excitation, a detection beam path and an illumination beam path, wherein the detection beam path images the sample on a detector and the illumination beam path illuminates the sample by way of structured illumination for exciting luminescence, wherein the illumination beam path comprises a device for realizing different illumination states, a computing and control device, which controls the microscope such that the sample is excited to luminescence by structured illumination such that the markers/molecules emit luminescent radiation blinking at a blinking rate, the illumination is structured such that the blinking rate varies locally and the sample is illuminated repeatedly in different illumination states of the structured illumination, such that a different local distribution of the blinking rate is obtained for each illumination state, the computing and control device reads the detector such that an image sequence of the luminescing sample is obtained in each of the different illumination states, the computing and control device generates a raw image from every image sequence, which reproduces the local distribution of the blinking rate, the computing and control device generates the high-resolution image, which has a spatial resolution greater than that of the image on the detector from the obtained raw images by computational processing comprising Fourier filtering.

The invention uses structured illumination in such a fashion that a local modulation of the blinking rate takes place in the sample. The purpose of said blinking rate modulation is to produce a higher resolution image, with the utilization of the principles known from the SIM method. In contrast to the known SIM principle, it is hence not a plurality of illumination states that are used, which differ with regard to the fluorescence intensity modulation, but illumination states are used instead, which differ with regard to the blinking rate modulation. Consequently, the abbreviation SBIM can be used to describe the concept according to the invention.

The sample is illuminated in different illumination states. The illumination states differ with regard to the blinking rate modulation they generate. To determine the blinking rate modulation for a given illumination state, an image sequence is recorded such that the images in each case show different blinking states, while the blinking rate modulation state is identical. The blinking rate modulation state is determined by means of appropriate evaluation of the image sequence. This represents a raw image. A raw image is generated from every blinking rate modulation state in this fashion. The plurality of raw images is subsequently converted into a high-resolution image in accordance with the known SIM concepts.

A blinking rate modulation (that is, an illumination state) can be retained for as long until the image sequence has been recorded. Alternatively, the image sequences for all blinking rate modulations (that is, all illumination states) can be assembled simultaneously, by cyclical alternation of the states.

Compared with the known SIM principle, the advantage of a greater increase in resolution is achieved, since the blinking properties of the majority of fluorophores can be influenced with considerably shorter wavelengths. Furthermore, the nonlinear computation of the fluorescence intensities brings about noise suppression when the raw images are generated.

The modulation of the blinking rate has been disclosed in the prior art. It is generally linearly dependent on the excitation intensity, such as it can be gathered from the publication by S. van de Linde et al., titled "Photoinduced formation of reversible dye radicals and their impact on super-resolution imaging", Photochem. Photobiol. Sci., 2011, 10, 499. Different methods can be used to read out the spatially resolved blinking rate (e.g. for each detector pixel), such as autocorrelation, frequency analysis (e.g. evaluation of a maximum in a previously defined frequency band that is characteristic for blinking rates of the dye).

The spatial information contained in the raw images, that is, the spatial dependence of the blinking rate, can be determined for example by way of frequency analysis. In the process, the mean blinking rate and/or amplitude is determined as an example. The raw image can contain for example gray scale values, which are assigned to the blinking rate or alternatively to the blinking amplitude.

As is known for the SIM principle, different illumination states, for example different rotary positions and longitudinal displacements of a blinking rate modulation structure, are required for the computation of the raw images. Alternatively, it is possible to work with a spot scanner according to the ISM principle.

Two-stage excitation can be used, depending on the markers or molecules in the samples. In that case, the fluorescence is excited first and the blinking rate is then modulated at a different wavelength.

If markers or sample molecules are used, which are statistically blinking independently from each other, i.e., in which the blinking of one molecule has no bearing on the blinking of the neighboring molecule, the raw image can also be generated by means of the method known from the SOFI concept, that is, by using a so-called cumulant-generating function.

To be able to select an image sequence that is as short as possible, it is preferable to select the recording of each individual image such that it is not greater than the reciprocal value of a mean blinking rate, preferably not greater than $1/10$ of the reciprocal value.

The structured illumination for modulating the blinking rate can be structured with regard to the radiation intensity. However, depending on the molecule, color structuring, i.e. structuring with regard to the wavelength distribution or structuring with regard to the polarization distribution is also possible.

To the extent characteristics of the SIM principle are used in the invention, the entire scope of disclosure of the following published documents involving details of the SIM principles are included herein: EP 1157297 B1, DE 19908883 A1, M. Gustafsson titled "Nonlinear structured-illumination microscopy: wide-field fluorescence imaging with theoretically unlimited resolution", Proc Natl Acad Sci USA, Sep. 13, 2005, 102 (37): 13081-6, Epub Sep. 2, 2005; R. Heintzmann and C. Cremer, (1998) Proc. SPIE Int. Soc. Opt. Eng. 3568, p. 185-195. The same applies to the ISM publication by C. Muller and J. Enderlein, titled "Image scanning microscopy", Physical Review Letters 104, 198101 (2010).

To the extent characteristics of the SOFI principle are used in the invention, the entire scope of the following publications relevant for this principle is included as well: T. Dertinger et al., "Fast, background-free, 3D super-resolution optical imaging fluctuation imaging (SOFI)", PNAS (2009), p. 22287-22292, along with related "supporting information"; "Achieving increased resolution and more pixels with Superresolution Optical Fluctuation Imaging (SOFI)", Opt. Express, Aug. 30, 2010, 18 (18): 18875-85, doi: 10.1364/IE.18.018875 and S. Geissbuehler et al., "Comparison between SOFI and STORM", Biomed. Opt. Express 2, p. 408-420 (2011).

According to the invention, the sample is provided with a marker, which emits statistically blinking luminescent radiation upon appropriate excitation. The term marker refers to ordinary labels or other substances that accumulate on the structures of the sample to be reproduced. Alternatively, a sample that is already appropriately luminescing can be used. Ultimately, a sample is hence microscopically imaged, which comprises structures that emit statically blinking luminescent radiation. "Statistically blinking" means that the individual markers or sample molecules are constantly switching between two luminescent radiation states, in each case independent of neighboring markers or molecules. In the simplest of cases, this can be a state in which luminescent radiation is emitted and a state in which no luminescent radiation is emitted. However, it is possible to switch between the emissions of two types of luminescent radiation that are different form one another, for example to switch between wavelengths, between polarizations, etc.

Based on an upgrade of the invention, it is preferred that the imaging speed and the blinking rate of the used molecules are adjusted to each other. On the one hand, this can be achieved with the selection of suitable marker or sample molecules. Obviously, it is also possible to adjust the blinking rate of the molecules by way of interaction. Depending on the molecule, this may involve different physical parameters, in particular temperature, wavelength of the illumination radiation acting as excitation radiation, intensity of the illumination radiation acting as excitation radiation, etc. Furthermore, chemical influences are possible, such as e.g. explained by Geissbuehler et al. Moreover, the imaging duration can be adjusted accordingly for a given blinking rate to achieve the state mentioned above.

To the extent the invention is described above or below with reference to methodical characteristics, this shall equally apply to the description of a corresponding microscope comprising the characteristics mentioned above. With regard to the microscope, it is integral that it's computational and control device allows a corresponding operation of the microscope for realizing the described methodical characteristics. The computational and control unit has an appropriate design for this purpose, for instance comprising a suitable programming unit. Obviously, the reverse applies in the event that individual characteristics are only described on the basis of the microscope. In that case, said characteristics shall apply analogously to the described microscopic methods.

As explained earlier, a rotation of the structured illumination is required for the SIM concept. It can be realized in a particularly simple fashion if an image field rotator is arranged behind the screen, which is positioned in the shared section of the second and third illumination beam path for the realization of said microscopic methods. Said image field rotator can be realized for example with an Abbe-Koenig prism.

It is understood that the characteristics mentioned above and to be explained below can be used not only in the specified combinations, but also in other combinations or alone, without leaving the scope of the present invention.

BRIEF DESCRIPTION OF THE DRAWINGS

The invention is explained in more detail below, for example based on the attached drawings, which likewise disclose characteristics that are relevant for the invention. In the figures.

DESCRIPTION OF THE EMBODIMENTS OF THE INVENTION

Figure 1:
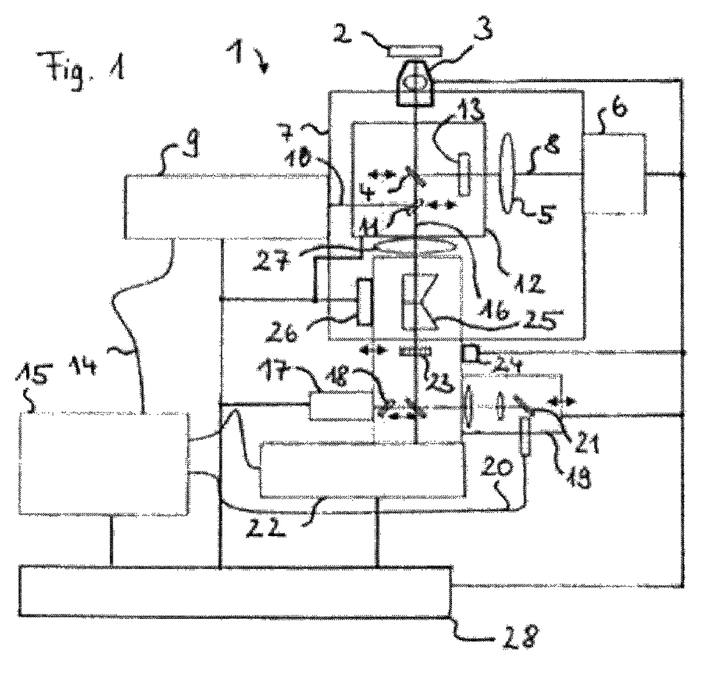
FIG. 1 shows a schematic representation of a combination microscope.

A microscope 1 is illustrated in FIG. 1, which is capable of simultaneously performing traditional microscopic methods, i.e., microscopic methods whose resolution is diffraction limited, and high-resolution microscopy methods, i.e., microscopic methods whose resolution is increased beyond the diffraction limit The microscope 1 is designed on the basis of a traditional laser scanning microscope and detects a sample 2. For this purpose, it comprises an objective 3, with the radiation for all microscopic methods running through it.

Together with a tube lens 5, the objective 3 images the sample on a CCD detector 6 by way of a beam splitter 4, said detector being a general flat panel detector in the example. Insofar, the microscope 1 comprises a conventional light-optical microscope module 7 and the beam path extending from the sample 2 through the objective 3 and the tube lens 5 to the CCD detector 6 corresponds to a conventional wide-field detection beam path 8. As indicated with the double arrow in FIG. 1, the beam splitter 4 is replaceable to allow a switch between beam splitters with different dichroic properties or achromatic beam splitters according to U.S. 2008/0088920.

Furthermore, a laser scanning module 9 is incorporated in the beam path to the objective 3, whose LSM illumination and detection beam path is coupled into the beam path to the objective 3 by way of a switchable mirror 11, which likewise has beam splitting functions. Hence, the beam path from the switchable mirror 11 to the objective 3 through the beam splitter 4 is a beam path, in which the illumination beam path and the detection beam path are combined. This applies both with respect to the laser scanning module 9 as well as with respect to the wide-field detection beam path 8, because, as will be explained later, illumination radiation is also coupled onto the switchable mirror 11, said illumination radiation realizing microscopic methods together with the wide-field detection beam path 8, i.e., the CCD detector 6.

The switchable mirror 11 and the beam splitter 4 are combined to form a beam splitter module 12, making it possible to exchange the switchable mirror 11 and the beam splitter 4 depending on the application. This is again illustrated with double arrows. Moreover, the beam splitter module 12 comprises an emission filter 13, which is positioned in the wide-field detection beam path 8 and appropriately filters the spectral parts that can propagate through the wide-field detection beam path 8. Obviously, the emission filter 13 in the beam splitter module 12 is also exchangeable.

The laser scanning module 9 obtains the laser radiation required for operation by way of an optical fiber 14 from a laser module 15.

In the design illustrated in FIG. 1, a collective illumination beam path 16 with illumination radiation for different microscopic methods flowing through it is coupled onto the beam splitter module 12, more precisely onto the switchable mirror 14. Different illumination beam paths of individual illumination modules are coupled into said collective illumination beam path 16. For example, a wide-field illumination module 17 couples wide-field illumination radiation into the collective illumination beam path 16 by way of a switchable mirror 18, such that the sample 2 is under wide-field illumination by way of a tube lens 27 and the objective 3. The wide-field illumination module can comprise for example an HBO arc lamp. A TIRF illumination module 19 is provided as an additional illumination module, used to realize TIRF illumination with a suitable position of the switchable mirror 18. For this purpose, the TIRF illumination module 19 obtains radiation from the laser module 15 by way of an optical fiber 20. The TIRF illumination module 19 comprises a mirror 21, which is longitudinally displaceable. As a result of the longitudinal displacement, the illumination beam emitted by the TIRF illumination module 19 is displaced perpendicular to the main direction of diffusion of the emitted illumination, with the result that the TIRF illumination on the objective 3 is incident onto the optical axis of the objective under an adjustable angle. The required angle of total reflection on the cover glass can easily be secured in this fashion. Obviously, other means are equally suitable to bring about said angle adjustment.

Furthermore, the illumination beam path of a manipulator module 22 is coupled onto the collective illumination beam path, said manipulator module likewise obtaining radiation from the laser module 15 by way of an optical fiber not described in more detail and guiding a punctiform or linear radiation distribution across the sample 2 by scanning. Therefore, the manipulator module 22 essentially corresponds to the illumination module of a laser scanning microscope and accordingly, the manipulator module 22 can also be operated in combination with the detector of the laser scanning module 9 or the wide-field detection of the CCD detector 6.

Furthermore, a screen 23 is provided in the collective illumination beam path 16, whose screen constant is below the limit frequency that can be transmitted into the sample 2 with the microscope 1. The screen 23 is diagonally displaceable to the optical axis of the collective illumination beam path 16. A corresponding displacement drive 24 is provided for this purpose.

An image filed rotator 25 rotated by a rotator drive 26 is additionally arranged in the collective illumination beam path 16 behind the screen in the direction of illumination. The image field rotator can for example be an Abbe-Koenig prism.

The modules and drives as well as detectors of the microscope 1 are all connected with a control device 28 by way of connections not described in detail. Said connection can be achieved for example with a data or control bus. The control device 28 controls the microscope 1 in different operating modes.

As a result, the control device 28 makes it possible to perform traditional microscopy on the microscope 1, i.e., wide-field microscopy (WF), laser scanning microscopy (LSM) as well as total internal reflection fluorescence (TIRF) microscopy. The microscope in FIG. 1 essentially comprises two modules suitable for laser scanning illumination, namely the laser scanning module 9 as well as the manipulator module 22. Obviously, other combinations are possible as well. Said modules are coupled onto the sample 2 with the objective 3 by way of tube lenses. The manipulator module 22 only comprises the excitation part of a laser scanning module, without the detection. As a result, the sample can be illuminated punctually and the illumination spot can be scanned across the sample 2. Preferably, the manipulator module 2 also comprises a switchable unit, e.g., a switchable lens or cylindrical lens used to switch between punctiform or linear illumination. Said linear illumination is advantageous in particular if the screen 23, which is present on an intermediate image of the collective illumination beam path 16, is swiveled in and positioned perpendicular to the line of the linear illumination.

Alternatively to the screen 23, a variably adjustable band modulator or a DMD can be used for generating structured illumination in the sample 2. In that case, the displacement drive 24 as well as the swiveling in and out of the screen 23 is obviously no longer required.

The image filed rotator 25 makes it possible to rotate the structured illumination generated by the screen 23 (or elements replacing it) around the optical axis of the collective illumination beam path 16, such that the structured illumination is present in different angles in the sample 2.

To switch between the individual operating modes, the switchable mirrors 18 and 11 as well as the beam splitter 4 are adjusted appropriately. This can be realized with the use of folding or swiveling mirrors such that the switch between the operating modes can be sequential. Alternatively, dichroic mirrors can be used, which allow the simultaneous operation of the different modules.

The beam splitter 4 is preferably designed as dichroic beam splitter, wherein the spectral properties can be adjusted such that spectral parts of the fluorescent emission of marker molecules to be detected by means of the CCD detector 6 reach the wide-filed detection beam path 8 and the other spectral components are transmitted to the greatest possible extent. To increase the flexibility with regard to the usability of marker molecules with different emission characteristics, a plurality of different exchangeable beam splitters 4 and emission filters 13 are arranged in the beam splitter module 12, e.g., on a filter wheel.

The microscope described above is now used to generate a high-resolution microscopic image. The control device 28 has a suitable design for this purpose, for example by comprising appropriate programming Before possible process sequences are explained based on FIGS. 4 and 5, essential characteristics and principles are first outlined based on FIGS. 2 and 3, which are integral components of the microscopic methods to be described.

Figure 2:
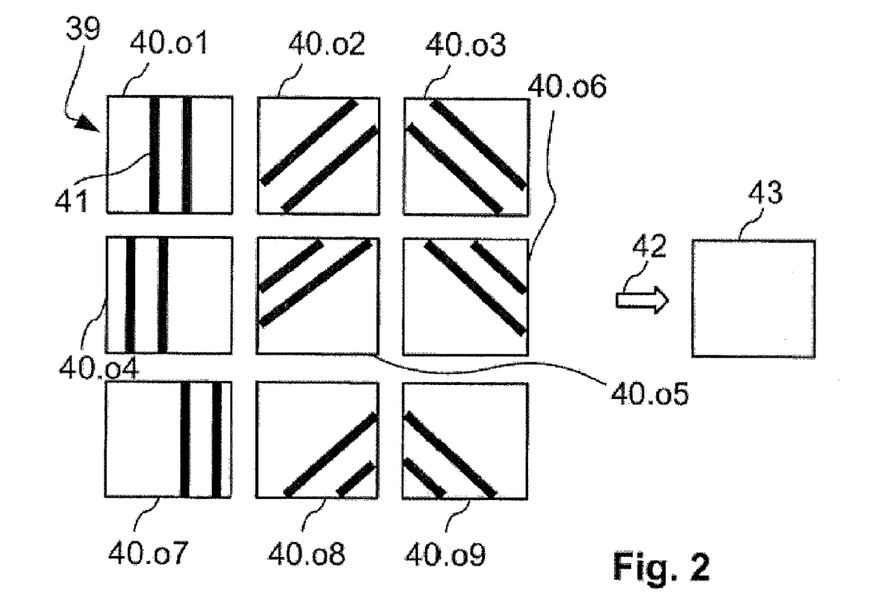
FIG. 2 shows a schematic representation to illustrate the generation of a high-resolution image from a plurality of raw images of a sample obtained from image sequences of different illumination states.

FIG. 2 contains an exemplary representation of the used concept for generating a higher resolution image. The sample that is microexamined in the microscope 1 of FIG. 1 is imaged repeatedly by wide-field irradiation, whereby different illumination states are set.

FIG. 2 shows a set 30 of individual raw images 40, which differ with regard to a structure 41 that is applied to the sample by way of suitable illumination by means of the illumination beam path 8. As can be seen, the structure 41 is different in the various raw images 40. The structure relates to a blinking rate of the fluorescent sample. A total of nine exemplary individual raw images 40 are available. This means that nine different orientations of the structure 41 are present. In the illustration of FIG. 2, the different structures are labeled with the addition of ".o1" to ".o9" to the reference number 40 of the respective raw image.

The structure relates to a modulation of the blinking rate. The individual raw images 40.x therefore differ with regard to different blinking rate structures. For example, a blinking rate that exceeds the white areas of a raw image 40.x may be present in the areas marked black.

The top view of the individual raw images 40.x shows that the nine orientations of the structure differ with regard to a displacement position and a rotary position. Obviously, greater numbers of different structures are also possible, such as it is known from the publications concerning the SIM principle listed in the general part of the description.

Figure 3:
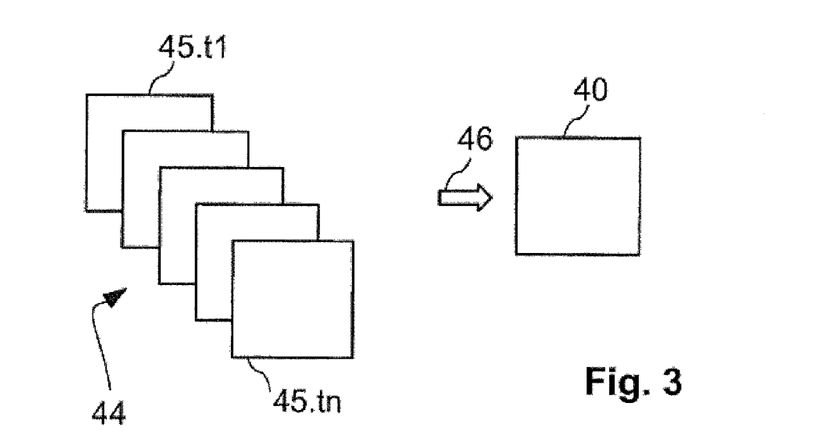
FIG. 3 shows a schematic representation to illustrate the generation of the image sequences of FIG. 2.

The generation of the individual raw images 40.x in set 39 is illustrated in FIG. 3. An image sequence 44 consisting of individual images 45.t1 to 45.tn is recorded for one orientation of the structure 41. In the process, the individual images 45.x are recorded over a period of time that is preferably short relative to the reciprocal value of a mean blinking rate of the sample molecules or used markers. Every image 45.x therefore represents an instantaneous blinking state. The image sequence 44 is recorded to determine the spatial distribution of the blinking rate. A raw image 40 is determined from the image sequence 44 by means of a blinking rate analysis 46, said raw image indicating the spatial distribution of the blinking rates (so-called blinking rate modulation structure). The raw image 40 can for instance be present as a gray-scale image, whose gray values are coding the blinking rate. Each of the individual raw images 40.o1 to 40.o9 is generated from an image sequence 44 in this fashion. The structure 41 is constant while an image sequence 44 is recorded.

A blinking rate analysis 46 can for example be a frequency analysis, which determines the corresponding blinking rate for each pixel from the image sequence 44 and/or the blinking amplitude. Alternatively, autocorrelation can be used, as it is known from the SOFI principle. A cumulant-generating function is a possible variant for the use of autocorrelation evaluation.

A high-resolution image 43 is then generated from the entire set 39, e.g., by means of Fourier transform 42.

Thus, FIG. 2 illustrates the characteristics of the SBIM principles. However, the shown structure 41 should be deemed purely exemplary. In particular, it is not compulsory for it to be a linear structure. Furthermore, the schematically drawn lines along the line can be structured further. Similarly, it is possible to use a scanned confocal spot illumination with confocal detection as disclosed in the publication by C. Muller and J. Enderlein, titled "Image scanning microscopy", Physical Review Letters, 104, 198101 (2010), rather than the linear structure used in the SIM publications mentioned above. Said principle is known as ISM. Rather than nine orientations of a structured illumination, an adequate plurality of individual images obtained by scanning a sample will be present in that case. Each image 40 then corresponds to a certain scanning position, i.e., a certain scanning state, while the image is being scanned.

Figure 4:
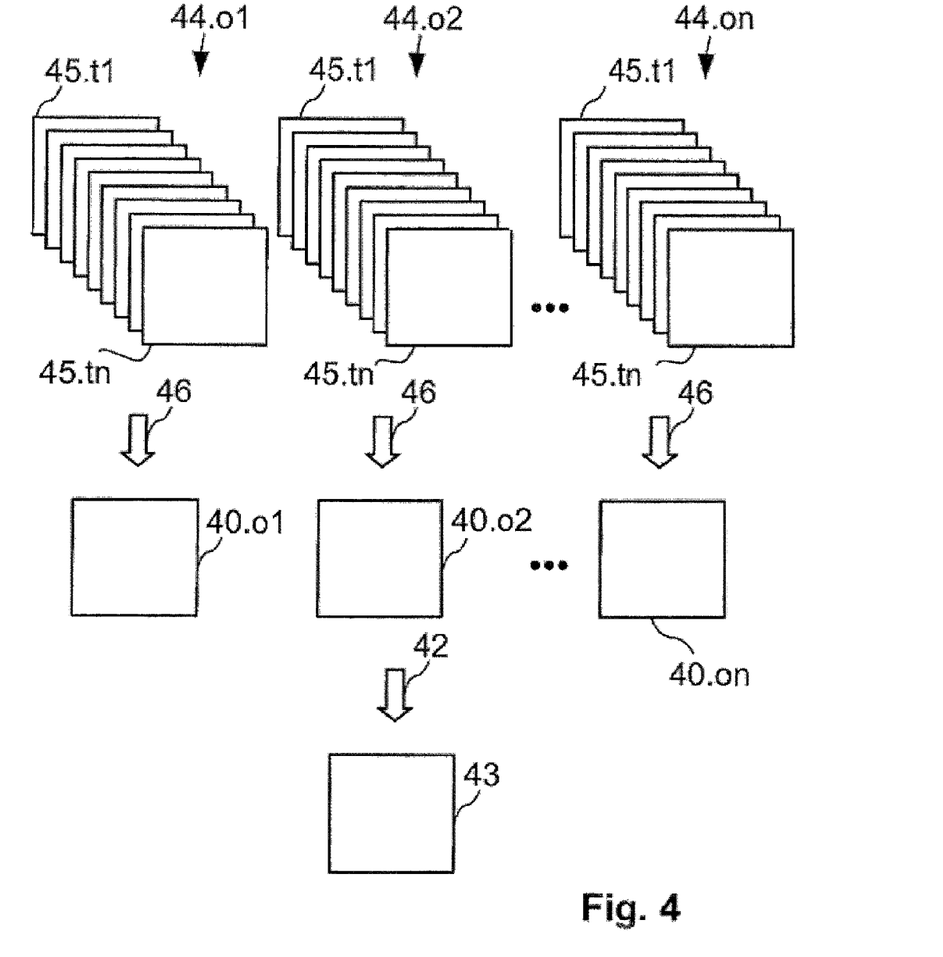
FIG. 4 shows a further schematic representation of a method for generating a higher resolution image.
Figure 5:
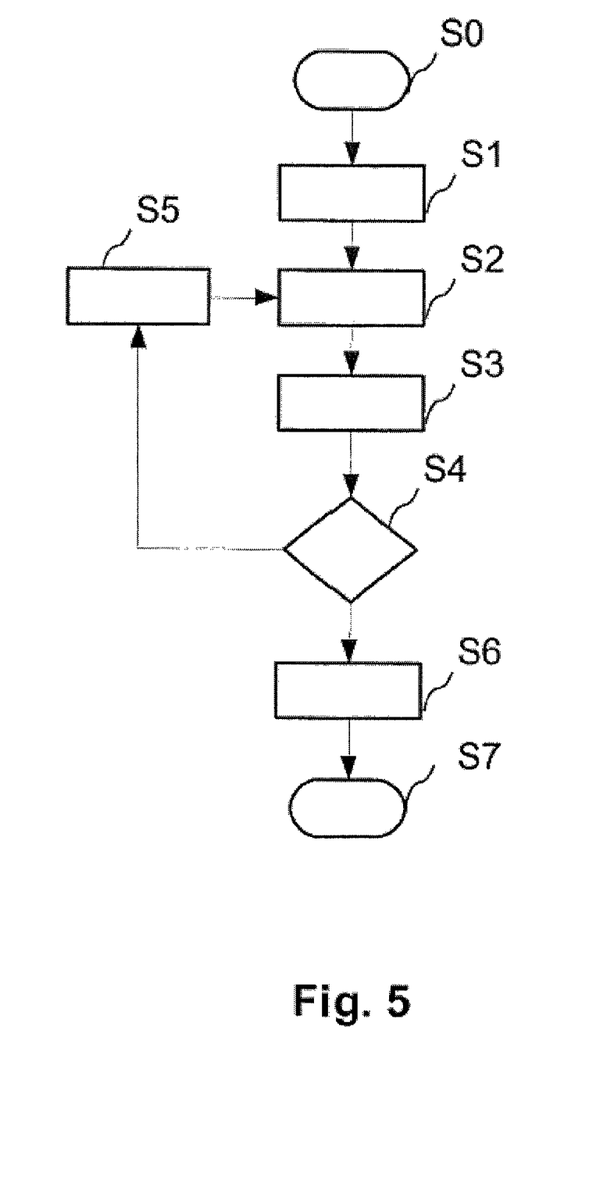
FIG. 5 shows a flow chart depicting the generation of a higher resolution image.

FIG. 4. shows a compilation of the sequence for generating the high-resolution image 43. The corresponding flow chart is illustrated in FIG. 5.

The procedure is started with step SO, which can comprise in particular the sample preparation, the provision of a sample with appropriate marker molecules, the pre-selection of appropriate marker molecules, etc.

Next, the sample is illuminated in a first illumination state in step 51, resulting in a first blinking rate modulation structure 41. A first image sequence 44 is subsequently recorded in step S2. Based on the blinking rate modulation state .o1, this relates to image sequence 44.o2 of FIG. 4. It consists of a time series of individual images 45.t1 to 45.tn.

The blinking rate analysis 45 is subsequently performed in step S3, to generate a corresponding raw image 40.o1 from the image sequence 44.o1, said raw image reproducing the first blinking rate structure .o1. Step S45 involves a query to find out if all blinking rate modulation structures intended for the further procedure have already been processed. If this is not the case, a jump is made to step S5, in which a change in the illumination state is set on the microscope 1, which brings about a different blinking rate modulation structure. In step S2, which is then performed again, the image sequence 44.o2 of FIG. 4 consisting of the individual images 44.t1 to 44.tn is subsequently recorded. This is followed by an analysis 46 for generating a raw image 40 in step S3, which in this case is the raw image 40.o2.

The loop comprising the steps S2, S3, S4 and S5 is repeated for as long until the predefined different structures 41 have been obtained. A corresponding number of raw images 40 will then be available, for example nine pieces, which differ with regard to the illumination state, i.e., the spatial position of a blinking rate modulation structure. As mentioned earlier, any structure that is known and suitable for the SIM or ISM principle can obviously be used for the blinking rate modulation structure.

The high-resolution image 43 is then generated in step S6 by way of appropriate computational compilation of the individual images 40.x, for example by means of Fourier analysis 42. The process is completed with step S7.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A microscopic method for generating a high-resolution image of a sample, wherein the method comprises the following steps:
a) providing said sample with multiple markers or molecules of the same type in an area of the sample which emit statistically blinking luminescent radiation upon excitation, said multiple markers or molecules being of a type whose blinking rate is dependent upon excitation intensity,
b) exciting said sample to luminescence by structured illumination such that said markers or said molecules emit luminescent radiation blinking at a blinking rate, wherein
the illumination is structured within said area such that in said area the blinking rate varies locally between markers or molecules of the same type according to a blinking rate modulation, and
the sample is repeatedly illuminated in different illumination states of the structured illumination, such that a different local distribution of the blinking rate is obtained for each illumination state,
c) repeatedly imaging said luminescing sample on a detector in each of the different illumination states, such that an image sequence is obtained for each of the different illumination states,
d) generating a raw image reproducing the local distribution of the blinking rate in said sample from each image sequence, and
e) generating a high-resolution image, which has a spatial resolution greater than that of the image on the detector from the obtained raw images by way of computational processing comprising Fourier filtering.

2. The method according to claim 1, wherein a mean blinking rate and/or blinking amplitude is determined with spatial resolution in step d).

3. The method according to claim 1, wherein a cumulant-generating function is used in step d) for generating the raw image, which evaluates the intensity fluctuations of each pixel in the image sequence caused by the blinking.

4. The method according to claim 1, wherein the recording duration of each image in step c) is selected such that it is not greater than a reciprocal value of a mean blinking rate.

5. The method according to claim 1, wherein the different illumination states comprise three rotary positions and at least three displacement positions of the structured illumination for each rotary position, and the sample is imaged on a flat panel detector having pixels.

6. The method according to claim 1, wherein the structured illumination is structured with regard to the radiation intensity.

7. The method according to claim 1, wherein the structured illumination is structured with regard to the wavelength.

8. The method according to claim 1, wherein the structured illumination is structured with regard to polarization.

9. A microscope for generating a high-resolution image of a sample, wherein the sample is provided with a marker that emits statistically blinking luminescent radiation after excitation, or a sample is used, which has molecules that emit statistically blinking luminescent radiation after excitation, comprising
a detection beam path and an illumination beam path, wherein the detection beam path images the sample on a detector and the illumination beam path illuminates the sample through structured illumination for exciting luminescence, wherein the illumination beam path comprises a device for realizing different illumination states,
a computing and control device, which controls the microscope such that
the sample having multiple markers or molecules of the same type in an area of the sample is excited to luminescence by structured illumination such that the markers or molecules emit luminescent radiation blinking at a blinking rate, said multiple markers or molecules being of a type whose blinking rate is dependent upon excitation intensity,
the illumination is structured within said area such that in said area the blinking rate varies locally between markers or molecules of the same type according to a blinking rate modulation, and
the sample is illuminated repeatedly in different illumination states of the structured illumination, such that a different local distribution of the blinking rate is obtained for each illumination state,
the computing and control device reads the detector such that an image sequence of the luminescing sample is obtained in each of the different illumination states,
the computing and control device generates a raw image from every image sequence, which reproduces the local distribution of the blinking rate, and
the computing and control device generates the high-resolution image, which has a spatial resolution greater than that of the image on the detector from the obtained raw images by computational processing comprising Fourier filtering.

10. The microscope according to claim 9, wherein the structured illumination is structured with regard to radiation intensity.

11. The microscope according to claim 9, wherein the structured illumination is structured with regard to the wavelength.

12. The microscope according to claim 9, wherein the structured illumination is structured with regard to polarization.

13. The microscope according to claim 9, wherein the sample or its one marker emits blinking luminescent radiation with an average blinking rate and the recording duration for each image is defined such that the duration to generate one set is not greater than the reciprocal value of the mean blinking rate.

14. The microscope according to claim 9, wherein the different illumination states comprise three rotary positions and at least three displacement positions of the structured illumination for each rotary position and the detection beam path images the sample on a planar detector comprising pixels.

15. The method according to claim 4, wherein said recording duration of each image in step c) is not greater than $\frac{1}{10}$ of the reciprocal value.

16. A microscope according to claim 13, wherein the recording duration for each image is defined such that the duration to generate one set is not greater than $\frac{1}{10}$ of the reciprocal value.

* * * * *

UNITED STATES PATENT AND TRADEMARK OFFICE
CERTIFICATE OF CORRECTION

PATENT NO.        : 9,726,877 B2                              Page 1 of 1
APPLICATION NO.   : 14/350919
DATED             : August 8, 2017
INVENTOR(S)       : Ingo Kleppe and Yauheni Novikau It is certified that error appears in the above-identified patent and that said Letters Patent is hereby corrected as shown below:

In the Specification

Column 1, Line 25:
Now reads: "copy,"
Should read: --copy.--

Column 9, Line 42:
Now reads: "comprising appropriate programming Before possible pro-"
Should read: --comprising appropriate programming. Before possible pro- --

Column 10, Line 59:
Now reads: "in step 51, resulting in a first blinking rate modulation"
Should read: --in step S1, resulting in a first blinking rate modulation--

Column 11, Line 8:
Now reads: "individual images 44.t1 to 44 tn is subsequently recorded."
Should read: --individual images 44.tl to 44 tn is subsequently recorded.--

Signed and Sealed this
Third Day of April, 2018

Andrei Iancu
*Director of the United States Patent and Trademark Office*